(12) United States Patent
Abhari et al.

(10) Patent No.: US 10,188,468 B2
(45) Date of Patent: Jan. 29, 2019

(54) FOCUSED BASED DEPTH MAP ACQUISITION

(71) Applicants: Kamyar Abhari, Toronto (CA); Gal Sela, Toronto (CA); Michael Frank Gunter Wood, Toronto (CA); Kai Michael Hynna, Toronto (CA); Tammy Kee-Wai Lee, Toronto (CA)

(72) Inventors: Kamyar Abhari, Toronto (CA); Gal Sela, Toronto (CA); Michael Frank Gunter Wood, Toronto (CA); Kai Michael Hynna, Toronto (CA); Tammy Kee-Wai Lee, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 53 days.

(21) Appl. No.: 15/506,228

(22) PCT Filed: Feb. 25, 2016

(86) PCT No.: PCT/CA2016/050189
§ 371 (c)(1),
(2) Date: Feb. 23, 2017

(87) PCT Pub. No.: WO2017/143427
PCT Pub. Date: Aug. 31, 2017

(65) Prior Publication Data
US 2018/0104009 A1    Apr. 19, 2018

(51) Int. Cl.
*A61B 1/00* (2006.01)
*G06T 7/00* (2017.01)
(Continued)

(52) U.S. Cl.
CPC .......... *A61B 34/20* (2016.02); *A61B 1/00009* (2013.01); *A61B 34/00* (2016.02);
(Continued)

(58) Field of Classification Search
CPC .............. A61B 1/00009; A61B 5/7425; A61B 2576/00; A61B 90/30; A61B 2090/365;
(Continued)

(56) References Cited

U.S. PATENT DOCUMENTS 5,231,443 A * 7/1993 Subbarao ................. G02B 7/28
396/93
5,305,092 A * 4/1994 Mimura ................. G01B 11/24
356/609

(Continued)

FOREIGN PATENT DOCUMENTS

EP        2967278 A1     1/2016
WO    WO 2011014421 A2 * 2/2011  ......... H04N 13/0235

*Primary Examiner* — John P Leubecker
(74) *Attorney, Agent, or Firm* — Ridout & Maybee LLP

(57) ABSTRACT

A medical navigation system is provided for acquiring a depth map of a surgical site of interest in a patient. The medical navigation system comprises a camera, a light projecting device, a display, and a controller. The controller has a processor coupled to a memory. The controller is configured to generate a signal provided to the light projecting device to project an edge indicator on the surgical site of interest, generate a signal to operate the camera to perform a focus sweep and capture a plurality of images during the focus sweep where the plurality of images includes the projected edge indicator, receive from the camera data representing the plurality of images captured during the focus sweep, and generate a depth map of the surgical site of interest using the data representing the plurality of images.

23 Claims, 10 Drawing Sheets

(51) Int. Cl.
  *A61B 34/20* (2016.01)
  *A61B 90/30* (2016.01)
  *A61B 34/00* (2016.01)
  *G06T 7/521* (2017.01)
  *A61B 34/10* (2016.01)
  *H04N 13/271* (2018.01)
  *H04N 5/272* (2006.01)
  *A61B 90/00* (2016.01)
  *A61B 17/34* (2006.01)

(52) U.S. Cl.
  CPC .............. *A61B 34/10* (2016.02); *A61B 90/30* (2016.02); *G06T 7/521* (2017.01); *H04N 5/272* (2013.01); *H04N 13/271* (2018.05); *A61B 17/3423* (2013.01); *A61B 90/37* (2016.02); *A61B 2034/107* (2016.02); *A61B 2034/2057* (2016.02); *A61B 2034/2065* (2016.02); *A61B 2090/365* (2016.02); *A61B 2090/366* (2016.02); *G06T 2207/10016* (2013.01); *G06T 2207/10021* (2013.01); *G06T 2207/10028* (2013.01); *G06T 2207/10048* (2013.01); *G06T 2207/10068* (2013.01); *G06T 2207/30016* (2013.01); *G06T 2207/30204* (2013.01)

(58) Field of Classification Search
  CPC ........ A61B 2090/355; A61B 2090/267; G06T 2207/10028; G06T 2207/10068; G06T 2207/30016; G06T 7/571; H04N 5/2356
  See application file for complete search history.

(56) References Cited

U.S. PATENT DOCUMENTS

| Patent / Publication | Date | Inventor | Classification |
|---|---|---|---|
| 6,229,913 B1* | 5/2001 | Nayar | G02B 27/2278 382/154 |
| 6,947,582 B1* | 9/2005 | Vilsmeier | G01B 11/24 345/419 |
| 8,405,742 B2* | 3/2013 | Lim | G06T 5/50 348/240.99 |
| 8,971,588 B2* | 3/2015 | Abramovich | G06K 9/00026 382/100 |
| 9,792,698 B2* | 10/2017 | Zhou | G06T 7/37 |
| 2007/0019883 A1* | 1/2007 | Wong | G06T 7/571 382/276 |
| 2008/0175576 A1* | 7/2008 | Hong | G03B 13/18 396/89 |
| 2009/0167923 A1* | 7/2009 | Safaee-Rad | H04N 5/23212 348/345 |
| 2009/0167930 A1* | 7/2009 | Safaee-Rad | G02B 7/38 348/347 |
| 2013/0222633 A1* | 8/2013 | Knight | H04N 5/23212 348/222.1 |
| 2013/0259315 A1* | 10/2013 | Angot | H04N 13/261 382/106 |
| 2014/0022352 A1* | 1/2014 | Fisker | G06T 5/003 348/46 |
| 2014/0211045 A1 | 7/2014 | Tanaka | |
| 2015/0279012 A1* | 10/2015 | Brown | G06T 5/003 382/284 |
| 2015/0347833 A1* | 12/2015 | Robinson | G01B 11/25 348/77 |
| 2016/0139243 A1* | 5/2016 | Send | G01S 7/4816 250/221 |
| 2016/0163053 A1* | 6/2016 | Tang | H04N 5/23222 348/135 |
| 2016/0182813 A1* | 6/2016 | Jouet | G06T 5/50 348/222.1 |
| 2016/0261844 A1* | 9/2016 | Kadambi | G01B 11/24 |
| 2016/0330360 A1* | 11/2016 | Powell | G01B 11/24 |
| 2016/0360091 A1* | 12/2016 | Lindskog | H04N 5/357 |
| 2017/0054962 A1* | 2/2017 | Zhou | G06T 7/0057 |
| 2018/0125338 A1* | 5/2018 | Pfeiffer | A61B 1/00172 |

* cited by examiner

FOCUSED BASED DEPTH MAP ACQUISITION

TECHNICAL FIELD

The present disclosure is generally related to image guided medical procedures, and more specifically to a system and method for scope based depth map acquisition.

BACKGROUND

The present disclosure is generally related to image guided medical procedures using a surgical instrument, such as an optical scope, an optical coherence tomography (OCT) probe, a micro ultrasound transducer, an electronic sensor or stimulator, or an access port based surgery.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon is aware of what is transpiring in the procedure and has an accurate depiction of the surgical site of interest on the monitor in front of him so that he understands where his tools are relative to the surgical site of interest.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO Brain Path. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body.

In the example of a port-based surgery, a straight or linear access port 12 is typically guided down a sulcal path of the brain. Surgical instruments would then be inserted down the access port 12. Optical tracking systems, used in the medical procedure, track the position of a part of the instrument that is within line-of-site of the optical tracking camera. Other tracking systems may be used, such as electromagnetic, optical, or mechanical based tracking systems.

Conventional systems have not offered good solutions for ensuring that a surgeon sees the surgical site of interest in enough detail. For example, when a port-based surgery is being performed, the surgeon's view down the access port is often restricted and the surgeon relies on a view of the surgical site of interest provided by a scope and shown on a display in the operating room. Conventionally, this view is a two dimensional image, which presents many limitations.

It would be desirable to have a system that helps a surgeon see the surgical site of interest and understand the 3 dimensional aspects of it. 3D depth information is beneficial for surgeons to use during surgical procedures as it improves tool manipulation within the surgical area of interest on a tissue of interest when viewing the field. In an example of endoscopic third ventriculostomy (ETV), surgeons may have a hard time to locate the basilar artery beneath the $3^{rd}$ ventricle if the tissue is thick and opaque. In those cases, 3D perception provides useful visual cues to identify the location of the artery and thus avoid injuring it. As such, it would be particularly desirable to provide 3D depth information when using a single camera that also provides visualization of the field.

SUMMARY

One aspect of the present disclosure provides a medical navigation system for acquiring a depth map of a surgical site of interest in a patient. The medical navigation system comprises a camera for viewing the surgical site of interest and having a depth of field and an adjustable focus, a light projecting device for projecting an edge indicator on the surgical site of interest, a display, and a controller electrically coupled to the camera, the light projecting device, and the display. The controller has a processor coupled to a memory. The controller is configured to generate a signal provided to the light projecting device to project the edge indicator on the surgical site of interest, generate a signal to operate the camera to perform a focus sweep and capture a plurality of images during the focus sweep such that substantially all elements of the surgical site of interest are in focus in at least one of the plurality of images, where the plurality of images includes the projected edge indicator, receive from the camera data representing the plurality of images captured during the focus sweep, and generate a depth map of the surgical site of interest using the data representing the plurality of images.

Another aspect of the present disclosure provides a method of acquiring a depth map of a surgical site of interest in a patient. The method is performed on a medical navigation system having a camera, a light projecting device, a display, and a controller electrically coupled to the camera, the light projecting device, and the display. The controller has a processor coupled to a memory. The method comprises projecting with the light projecting device an edge indicator on the surgical site of interest, performing with the camera a focus sweep and capturing a plurality of images during the focus sweep such that substantially all elements of the surgical site of interest are in focus in at least one of the plurality of images, where the plurality of images includes the projected edge indicator, receiving at the controller from the camera data representing the plurality of images captured during the focus sweep, and generating a depth map of the surgical site of interest using the data representing the plurality of images.

Another aspect of the present disclosure provides a medical navigation system for acquiring a depth map of a surgical site of interest in a patient. The medical navigation system comprises a camera for viewing the surgical site of interest, a light projecting device for projecting an edge indicator on the surgical site of interest, the light projecting device having an adjustable focus plane, a display, and a controller electrically coupled to the camera, the light projecting device, and the display. The controller has a processor coupled to a memory. The controller is configured to generate a signal provided to the light projecting device to project the edge indicator on the surgical site of interest and perform a focus sweep of the light projecting device over a range of the adjustable focus plane, the surgical site of interest having a surface contour with a maximum elevation and a minimum elevation and the sweep of the adjustable focus plane spanning a range from the minimum elevation to the maximum elevation, generate a signal to operate the camera and capture a plurality of images during the focus sweep of the light projecting device, the plurality of images including the projected edge indicator, receive from the camera data representing the plurality of images captured during the focus sweep, and generate a depth map of the surgical site of interest using the data representing the plurality of images.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
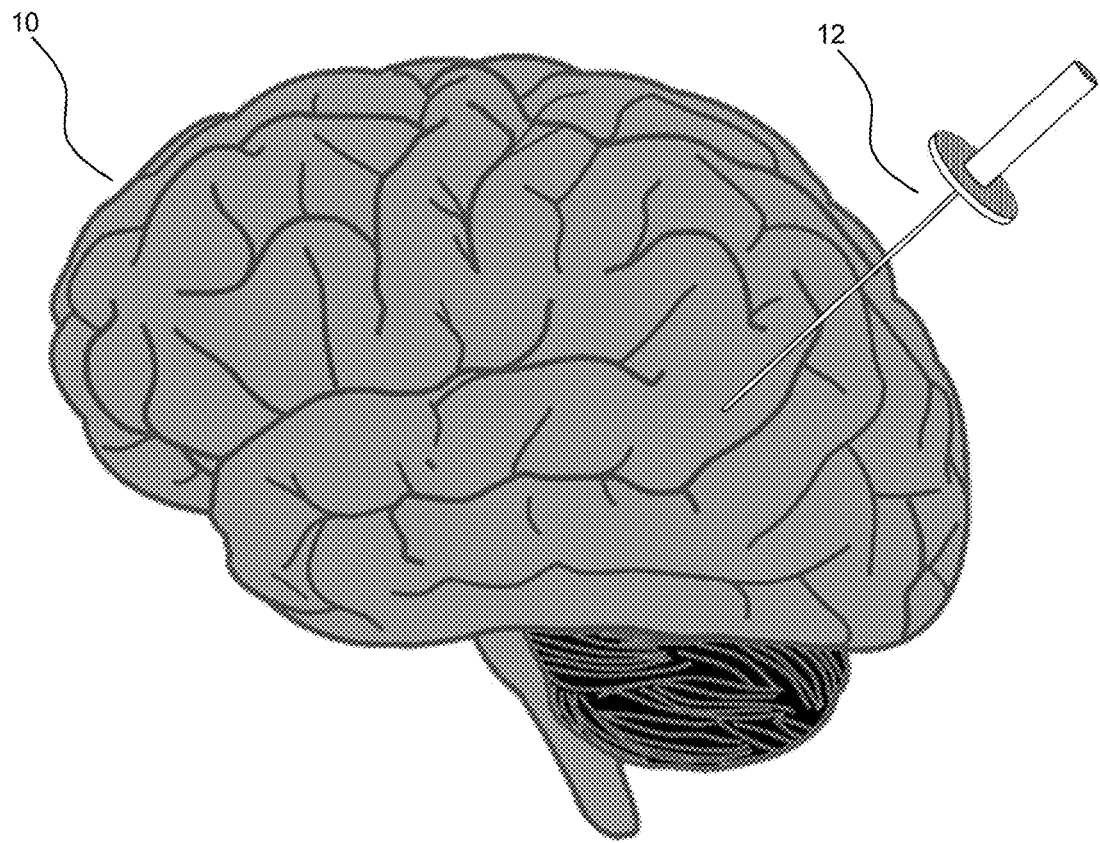
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g., minimally invasive medical procedures) are performed based on access to internal tissue through the access port.

Figure 2:
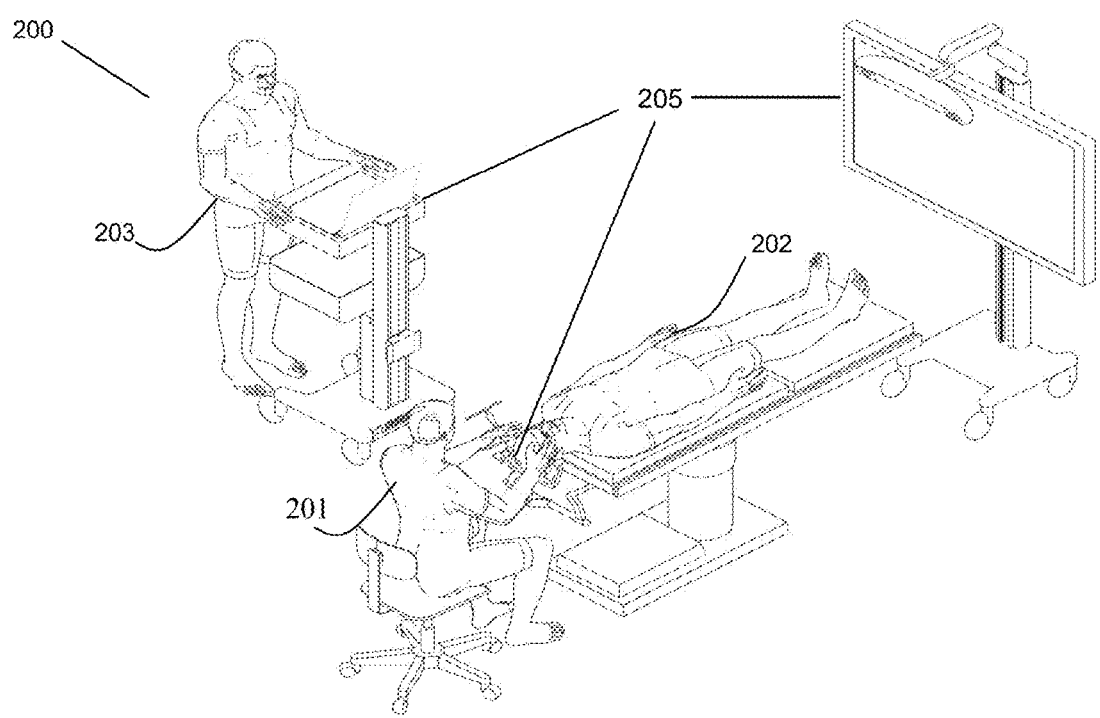
FIG. 2 shows an exemplary navigation system to support minimally invasive surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
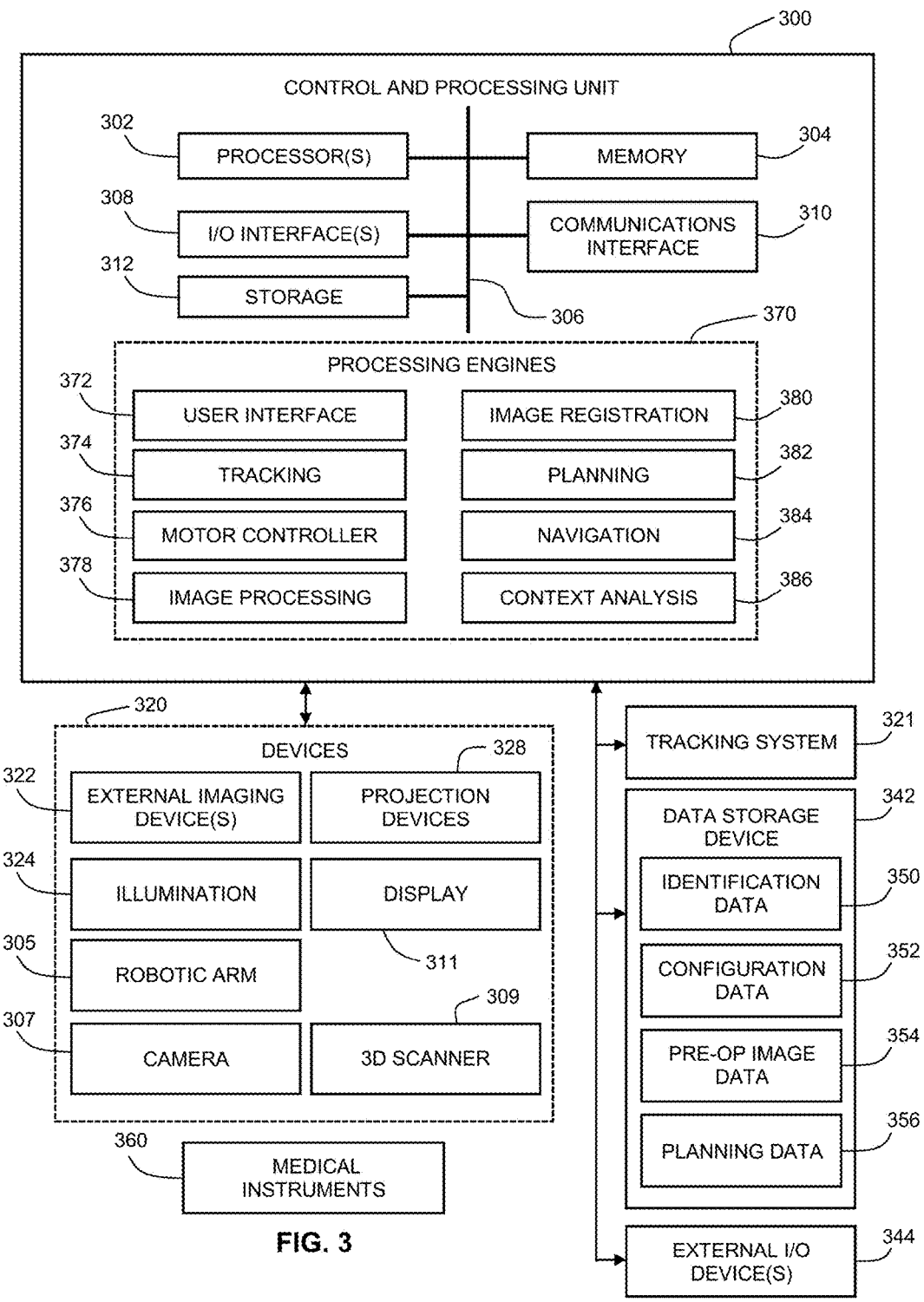
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 205 shown in FIG. 3 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300. In another example, camera 307 may be a video camera.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, and one or more displays 311, and a scanner 309, which in one example may be a three dimensional (3D) scanner.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
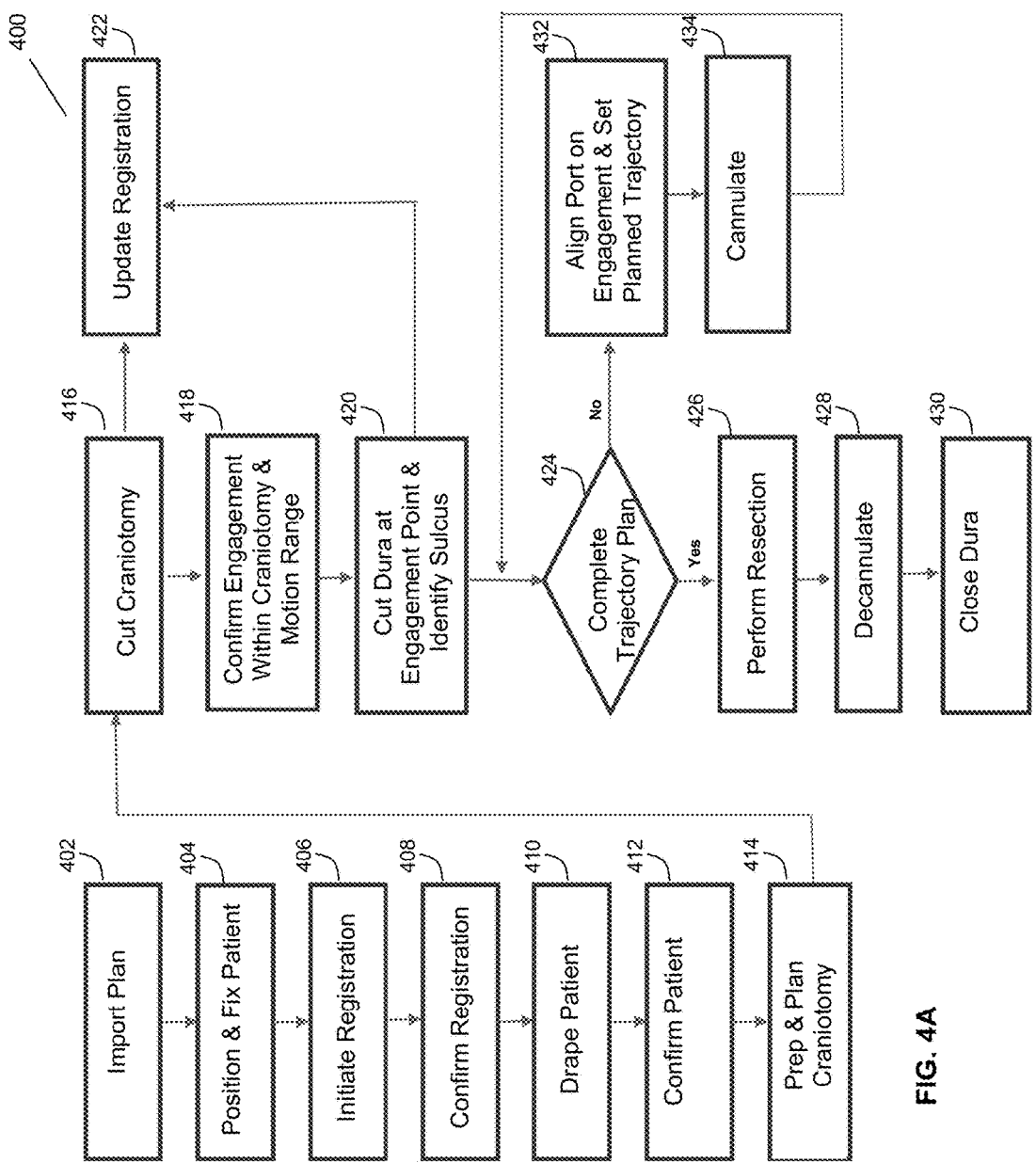
FIG. 4A is a flow chart illustrating a method involved in a surgical procedure using the navigation system of FIG. 2.

Referring to FIG. 4A, a flow chart is shown illustrating a method 400 of performing a surgical procedure using a navigation system, such as the medical navigation system 205 described in relation to FIG. 2. At a first block 402, the surgical plan is imported.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower of medical navigation system 205.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
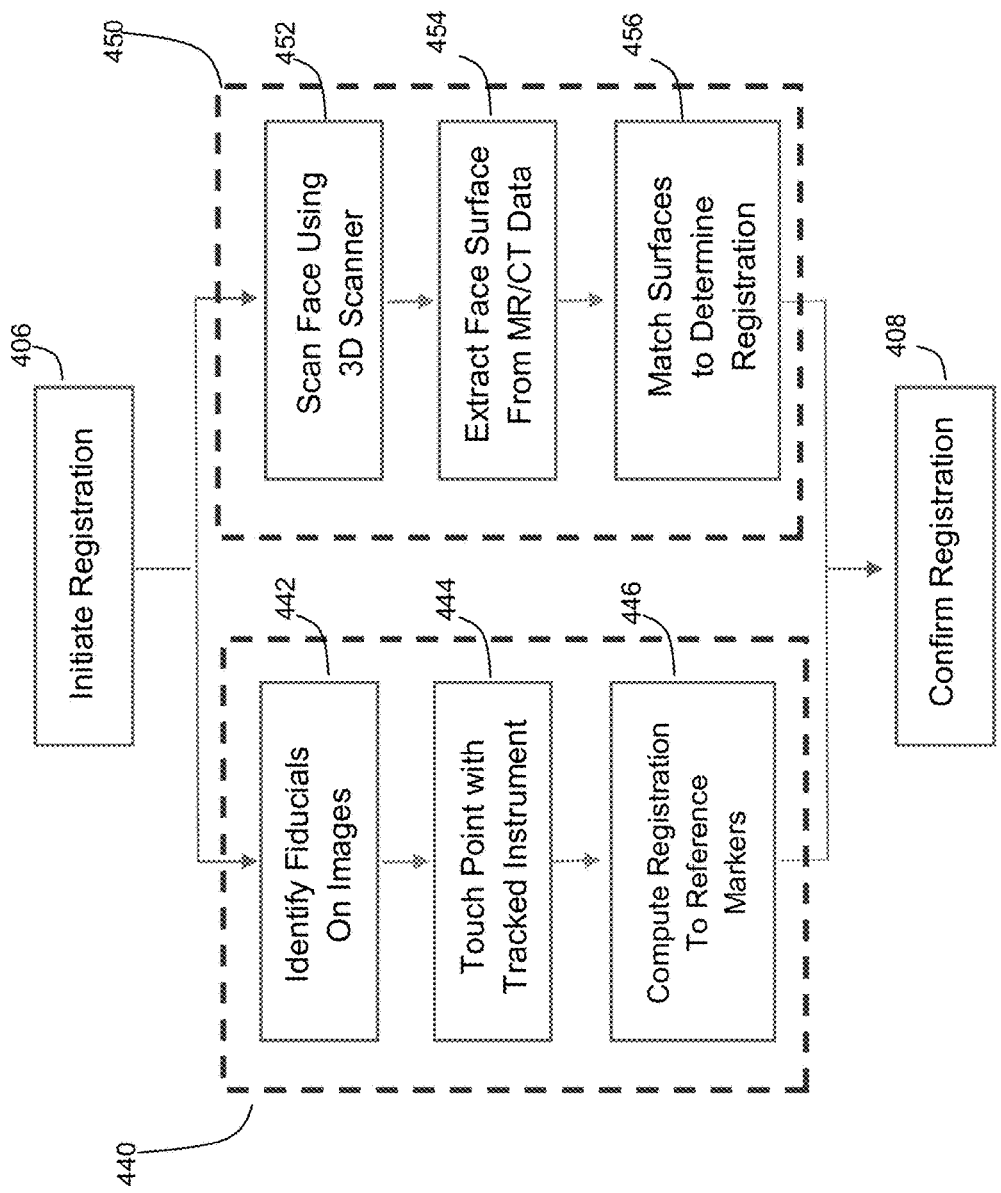
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4B.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
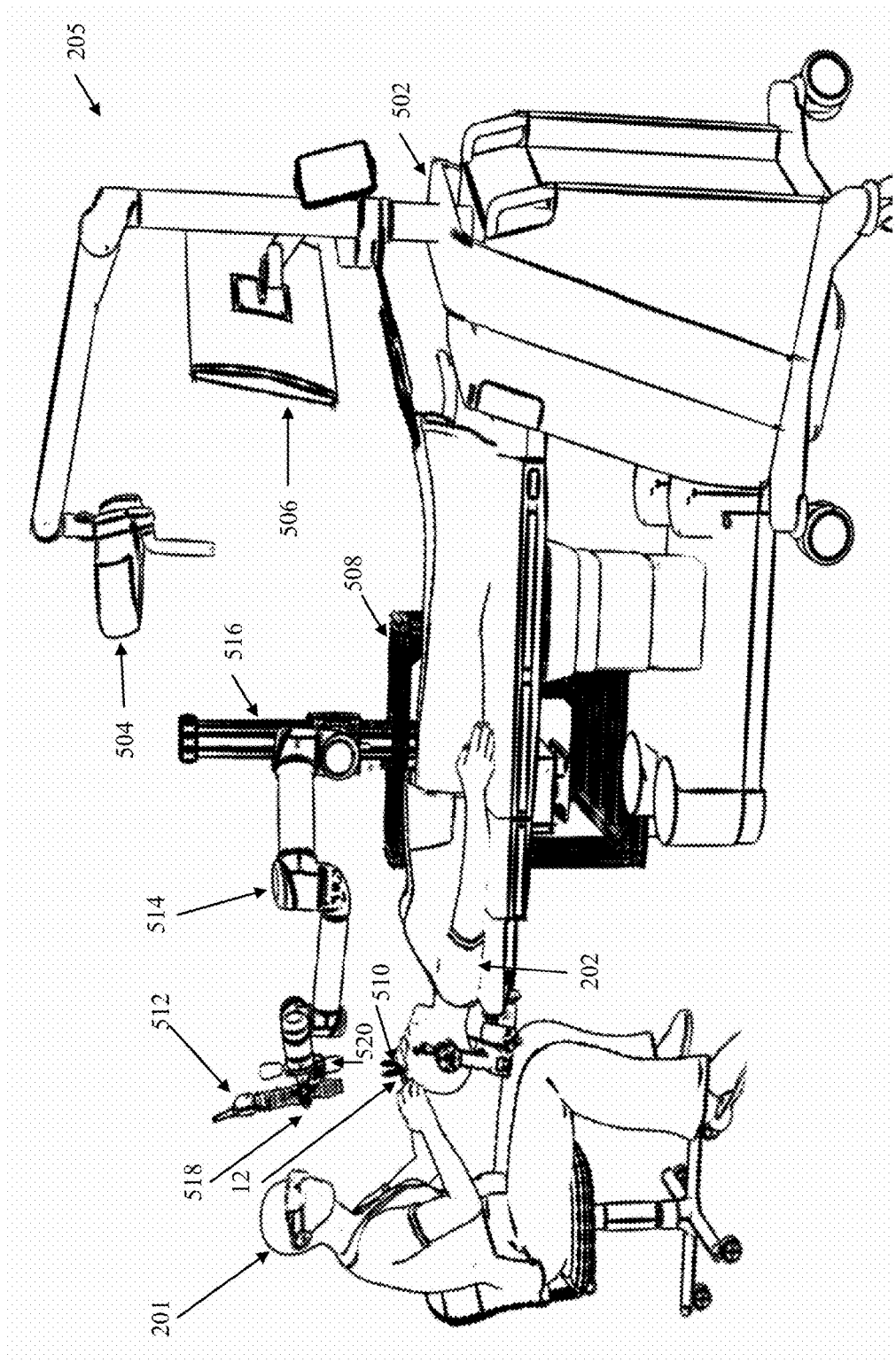
FIG. 5 is an exemplary navigation system similar to FIG. 2 illustrating system components of an exemplary surgical system that may be used for acquiring a depth map of a surgical site of interest.

FIG. 5 is a diagram illustrating components of an exemplary surgical system that is similar to FIG. 2. FIG. 5 illustrates a navigation system 205 having an equipment tower 502, tracking system 504, display 506, an intelligent positioning system 508 and tracking markers 510 used to track instruments or an access port 12. Tracking system 504 may also be considered an optical tracking device, tracking camera, video camera, 3D scanner, or any other suitable camera or scanner based system. In FIG. 5, a surgeon 201 is performing a tumor resection through a port 12, using an imaging device 512 (e.g., a scope and camera) to view down the port at a sufficent magnification to enable enhanced visibility of the instruments and tissue. The imaging device 512 may be an external scope, videoscope, wide field camera, or an alternate image capturing device. The imaging sensor view is depicted on the visual display 506 which surgeon 201 uses for navigating the port's distal end through the anatomical region of interest.

An intelligent positioning system 508 comprising an automated arm 514, a lifting column 516 and an end effector 518, is placed in proximity to patient 202. Lifting column 516 is connected to a frame of intelligent positioning system 508. As seen in FIG. 5, the proximal end of automated mechanical arm 514 (further known as automated arm 514 herein) is connected to lifting column 516. In other embodiments, automated arm 514 may be connected to a horizontal beam, which is then either connected to lifting column 516 or directly to frame of the intelligent positioning system 508. Automated arm 514 may have multiple joints to enable 5, 6 or 7 degrees of freedom.

End effector 518 is attached to the distal end of automated arm 514. End effector 518 may accommodate a plurality of instruments or tools that may assist surgeon 201 in his procedure. End effector 518 is shown as holding an external scope and camera, however it should be noted that this is merely an example and alternate devices may be used with the end effector 518 such as a wide field camera, microscope and OCT (Optical Coherence Tomography), video camera, 3D scanner, or other imaging instruments. In another example, multiple end effectors may be attached to the distal end of automated arm 518, and thus assist the surgeon 201 in switching between multiple modalities. For example, the surgeon 201 may want the ability to move between microscope, and OCT with stand-off optics. In a further example, the ability to attach a second, more accurate, but smaller range end effector such as a laser based ablation system with micro-control may be contemplated.

In one example, the intelligent positioning system 508 receives as input the spatial position and pose data of the automated arm 514 and target (for example the port 12) as determined by tracking system 504 by detection of the tracking markers on the wide field camera on port 12. Further, it should be noted that the tracking markers may be used to track both the automated arm 514 as well as the end effector 518 either collectively or independently. It should be noted that a wide field camera 520 is shown in FIG. 5 and that it is connected to the external scope (e.g., imaging device 512) and the two imaging devices together are held by the end effector 518. It should additionally be noted that although these are depicted together for illustration of the diagram that either could be utilized independently of the other, for example where an external video scope can be used independently of the wide field camera 520.

Intelligent positioning system 508 computes the desired joint positions for automated arm 514 so as to maneuver the end effector 518 mounted on the automated arm's distal end to a predetermined spatial position and pose relative to the port 12. This redetermined relative spatial position and pose is termed the "Zero Position" where the sensor of imaging device 512 and port 12 are axially alligned.

Further, the intelligent positioning system 508, optical tracking device 504, automated arm 514, and tracking markers 510 may form a feedback loop. This feedback loop works to keep the distal end of the port 12 (located inside the brain) in constant view and focus of the end effector 518 given that it is an imaging device as the port position may be dynamically manipulated by the surgeon during the procedure. Intelligent positioning system 508 may also include a foot pedal for use by the surgeon 201 to align the end effector 518 (i.e., holding a videoscope) of automated arm 514 with the port 12.

Figure 6:
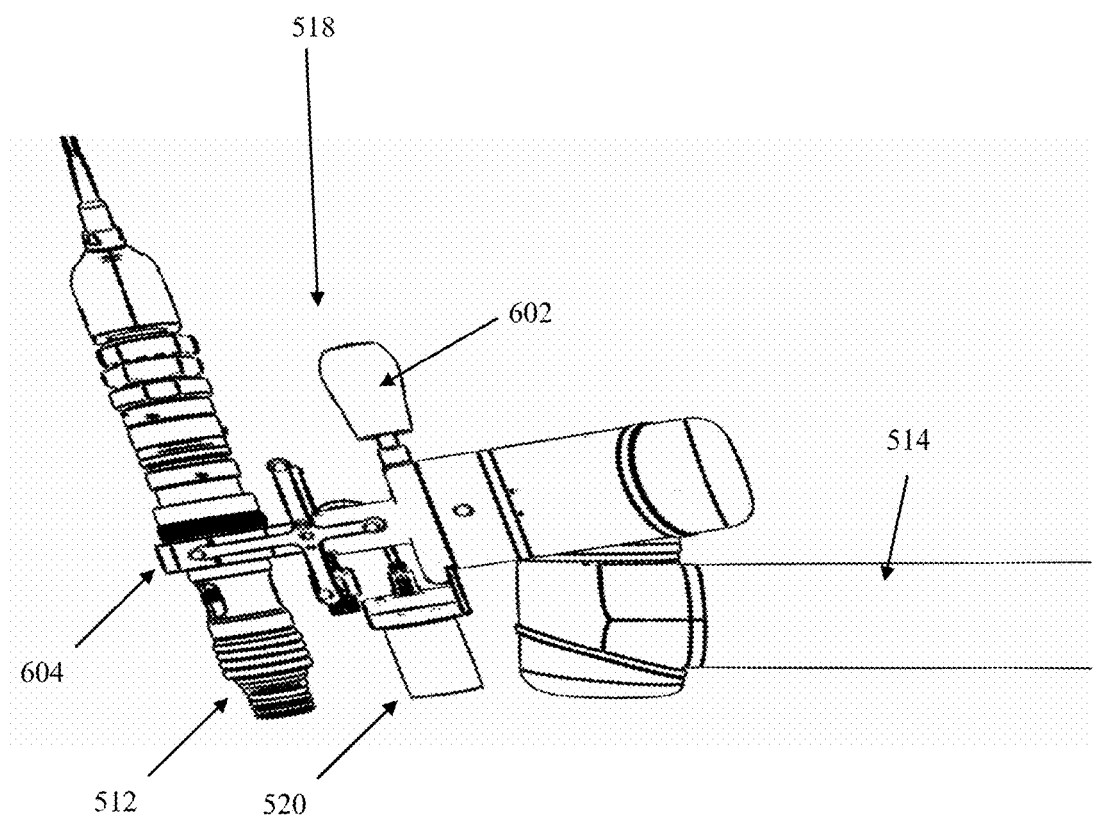
FIG. 6 is perspective drawing illustrating a conventional end effector holding a camera.

Referring to FIG. 6, a conventional end effector 518 is shown attached to automated arm 514. The end effector 518 includes a handle 602 and a scope clamp 604. The scope clamp 604 holds imaging device 512. The end effector also has wide field camera 520 attached thereto, which in one example could be a still camera, video camera, or 3D scanner used to monitor muscles of the patient for movement, tremors, or twitching.

The depth of field (DOF) may be defined as the distance between the nearest and farthest elements in the camera's field-of-view that appear in focus in an image. In one aspect of the present description, the DOF and the midpoint between the "near" and "far" edges (e.g., the working distance) are controlled by the optics of the scope system, such as imaging device 512, and by determining what sections of an image are in focus, where the distance or depth of those sections from the scope can be extracted or calculated. By changing the working distance and analyzing the change in focus, a depth-map of the scene can be created. Narrowing the DOF may be used to increase the resolution in depth.

In one example, acquisition of a depth map may be facilitated by using a combination of focus and grid projection to improve feature differentiation on soft structures with unclear delineation of boundaries. This method extracts depth information by looking at the image sharpness within the neighborhood of interest. This method may perform poorly when features are not distinguishable within the aforementioned neighborhood. Projecting a grid onto the surface introduces new features for such analysis, improving the result.

In another example, an intelligent scanning process for depth map acquisition may be applied including an optimization of focus scanning protocol. One of the simplest approaches involves linearly stepping the working distance of the imaging device 512 over a fixed range and analyzing the image focus at each stepped position. In some cases this approach may be suboptimal as time is wasted on capturing and analyzing working distances where there is no relevant information. Some combination of intelligent working distance positioning as well as using multiple DOFs to determine where relevant surfaces are may speed up the scanning process. In one example, a dual scope full field adaptive microscope (FFAM) for 3D imaging may be used, which can produce both a narrow field of view (NFOV) and/or a wide field of view (WFOV).

In another example, stereoscopic disparity information based on two separate scopes may be used to produce stereoscopic vision to generate a depth map of the surgical scene. One possible advantage of this method over the motorized focus is that this method may be performed in real-time and so does not interrupt the surgery for collecting data. One scope and focus approach may be used to acquire depth while the other may be used to acquire visual imaging of the scene with no blurring.

Figure 7:
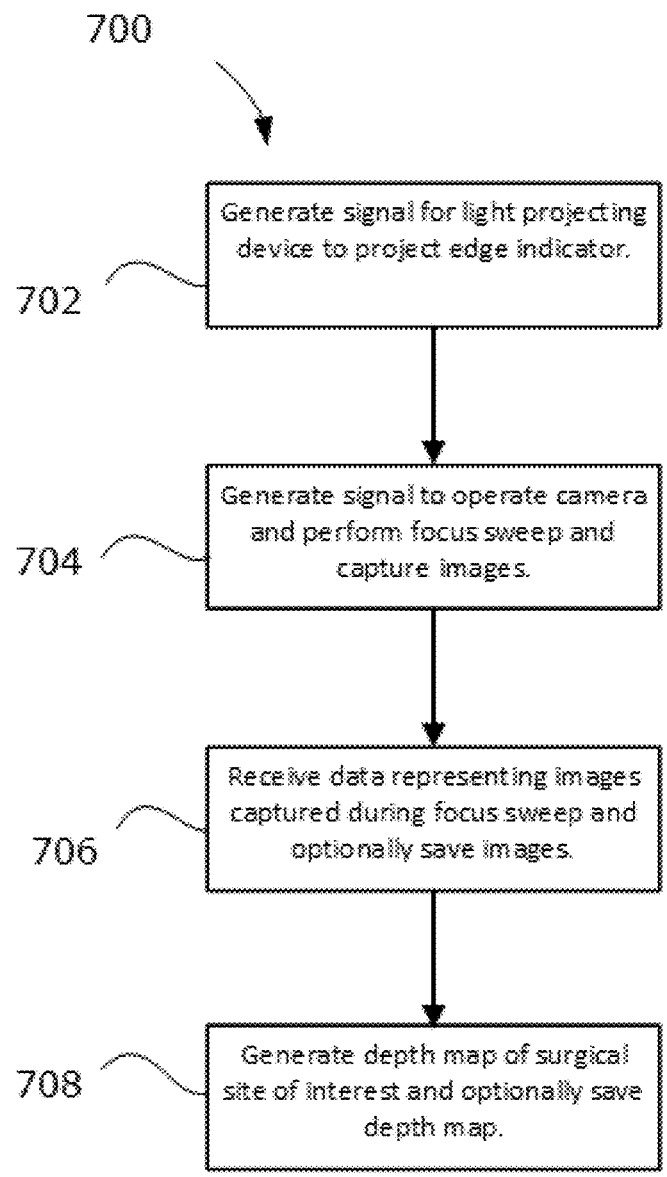
FIG. 7 is a flow chart illustrating a method for acquiring a depth map of a surgical site of interest in a patient according to one aspect of the present description.

Referring now to FIG. 7, a flow chart is shown illustrating a method 700 for acquiring a depth map of a surgical site of interest in a patient according to one aspect of the present description. The method 700 may be executed using a medical navigation system, such as the medical navigation system 205. The medical navigation system may have a camera, such as the camera 307 and/or imaging device 512 and/or wide field camera 520, for viewing the surgical site of interest. The camera has a depth of field (DOF) and an adjustable focus. The medical navigation system may further have a light projecting device for projecting an edge indicator on the surgical site of interest, a display, such as the display 506, and a controller, such as the controller 300, electrically coupled to the camera, the light projecting device, and the display. The controller has a processor, such as the processor 302, coupled to a memory, such as memory 304 and/or the data storage device 342. The controller is configured to execute at least part of the method 700.

At a first block 702, the method 700 generates a signal, for example by controller 300, provided to the light projecting device to project the edge indicator on the surgical site of interest. In one example, the projected edge indicator is projected using either visible light or invisible light, such as infrared light or ultraviolet light.

Figure 8:
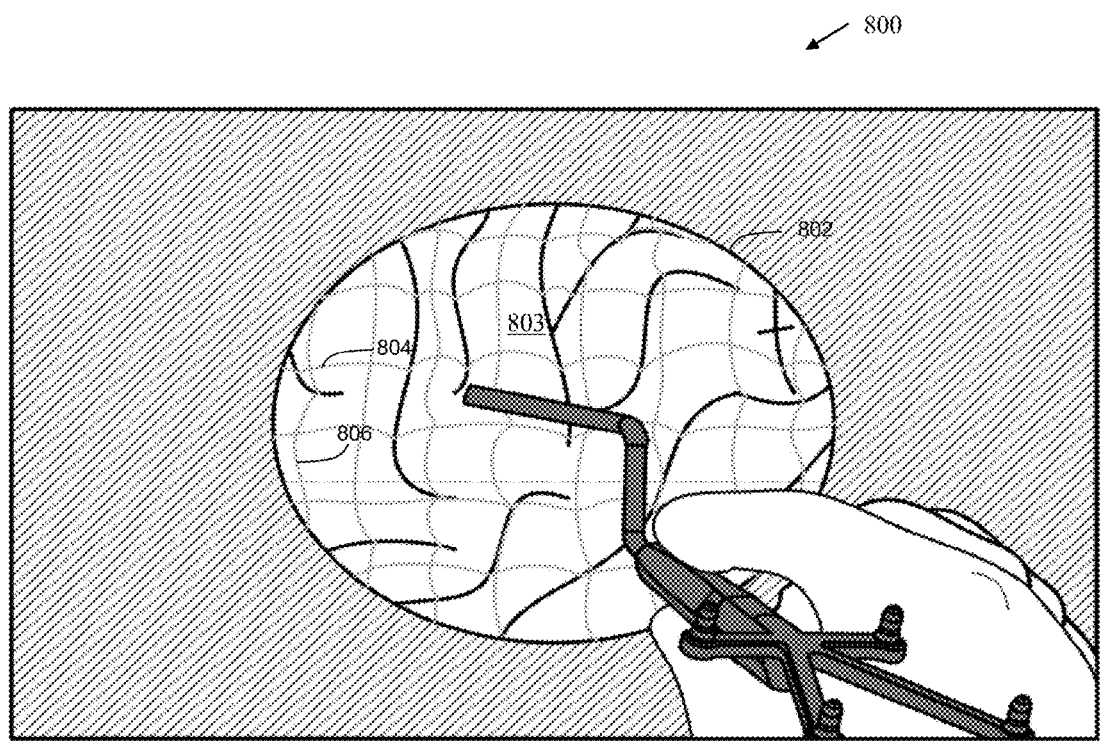
FIG. 8 is a diagram illustrating an exemplary surgical field of view including an exemplary edge indicator.

Referring to FIG. 8, a diagram is showing illustrating an exemplary surgical field of view including an edge indicator, indicated by reference 800. FIG. 8 shows an exemplary field of view 802 captured by the camera showing a surgical site of interest 803. In one example, the projected edge indicator may include a plurality of horizontal parallel lines 804 and a plurality of vertical parallel lines 806 each perpendicular to the plurality of horizontal parallel lines 804, where the plurality of horizontal parallel lines 804 and the plurality of vertical parallel lines 806 are arranged in a grid pattern. While the plurality of horizontal parallel lines 804 may not appear perfectly parallel to each other and the plurality of vertical parallel lines 806 may not appear may not appear perfectly parallel to each other, the lines are projected as parallel but conform to the surface onto which they are projected in the surgical site of interest, therefore not necessarily appearing parallel. Likewise, while the plurality of horizontal parallel lines 804 and the plurality of vertical parallel lines 806 may not appear perfectly perpendicular to each other, they are projected as perpendicular but conform to the surface onto which they are projected in the surgical site of interest, therefore not necessarily appearing perpendicular. While a grid pattern is given as an example, any arrangement of lines or other indicators may be used. The lines need not necessarily be perfectly parallel or perpendicular to each other and need not be lines at all. The objective of the projected edge indicator is that some known formation of indicators is projected onto the surgical site of interest that allows the camera and controller to assess the focus at various focus depths, as discussed further below, and any suitable edge indicator may be used according to the design criteria of a particular application.

Returning to FIG. 7, next, at a block 704, a signal is generated, for example by controller 300, to operate the camera to perform a focus sweep and capture a plurality of images during the focus sweep such that most or substantially all elements of the surgical site of interest are in focus in at least one of the plurality of images. The plurality of images includes the projected edge indicator, which may be useful for later analysis. Any number of images may be captured according to design criteria of a particular application. In some examples, 5-10 images may be enough over steps of the working distance, while in other applications hundreds or thousands of images may be useful.

In an alternate example to the block 704, a signal may be generated and provided to the light projecting device to project the edge indicator on the surgical site of interest and perform a focus sweep of the light projecting device over a range of the adjustable focus plane. The surgical site of interest may have a surface contour with a maximum elevation and a minimum elevation and the sweep of the adjustable focus plane may span a range from the minimum elevation to the maximum elevation. In other words, in an alternate example, it may be the edge indicator projector that performs a focus sweep of the edge indicator as opposed to the camera, which in this example may remain stationary while the plurality of images are captured.

Next, at a block 706, data is received from the camera, for example by controller 300, representing the plurality of images captured during the focus sweep. The data representing the plurality of images may be saved in the memory, such as the memory 304.

Next, at a block 708, a depth map of the surgical site of interest is generated, for example by controller 300, using the data representing the plurality of images. The generated depth map may be saved in the memory, such as the memory 304.

In one example, the controller may be further configured to generate a signal to operate the camera (e.g., either the same camera 307 and/or imaging device 512 and/or wide field camera 520 or another one of these cameras or imaging devices) to capture a live video feed of the surgical site of interest while a surgical procedure is being performed. Data may be received from the camera representing the live video feed and the live video feed may be displayed on the display. Further, the depth map may be displayed on the display overlaid on the live video feed. In one example, the depth map includes a series of contour lines that show relative elevations of the surgical site of interest.

In one example, the depth map of the surgical site of interest may be generated using the data representing the plurality of images by analyzing image sharpness of features of each of the plurality of images based on the focus depth of each of the plurality of images. In one example, analyzing sharpness of intersecting perpendicular and horizontal lines in the grid pattern in the plurality of images may provide information as to when a particular area surrounding an intersection of lines is in focus. In another example, the depth map of the surgical site of interest may be generated by analyzing polarization of light reflected from the surgical site of interest.

In another example, the light projecting device for projecting an edge indicator on the surgical site of interest may be entirely optional and an edge indicator may not be needed. In this example, an object being scanned may have sufficient edge contrast such that the edge indicator is not needed and the edges of the object may be examined directly at the block 708.

In one example, the focus sweep is performed in response to an input provided to the controller using an input device coupled to the controller, such as using any of the external I/O devices 344 such as a keyboard, mouse, foot pedal, etc. In another example, the light projecting device may be configured to project the light through the camera, such as through the camera 307 and/or imaging device 512 and/or wide field camera 520, such that the edge indicator is projected through the same optical system used by the camera for viewing the image. In one example, the light projecting device may be integrated into the camera. In one example, the camera includes a videoscope.

In yet other examples, the edge indicator may be projected using a laser grid and/or contrast agents may be applied to the surgical site of interest to create more contrast. In another example, an agent such as PpIX may be injected into the patient and get to the surgical site through the bloodstream. Any suitable technique may be applied to create enough contrast or improve the contrast to achieve the desired depth of focus to facilitate the method 700. In another example, the method 700 may find the depth of focus that produces sharpest image for every single pixel of one or more of the captured images, or most of the pixels of one or more of the captured images. In one example, the system and method of the present application may be able to achieve a depth resolution in the order of one millimeter, or even better.

Figure 9:
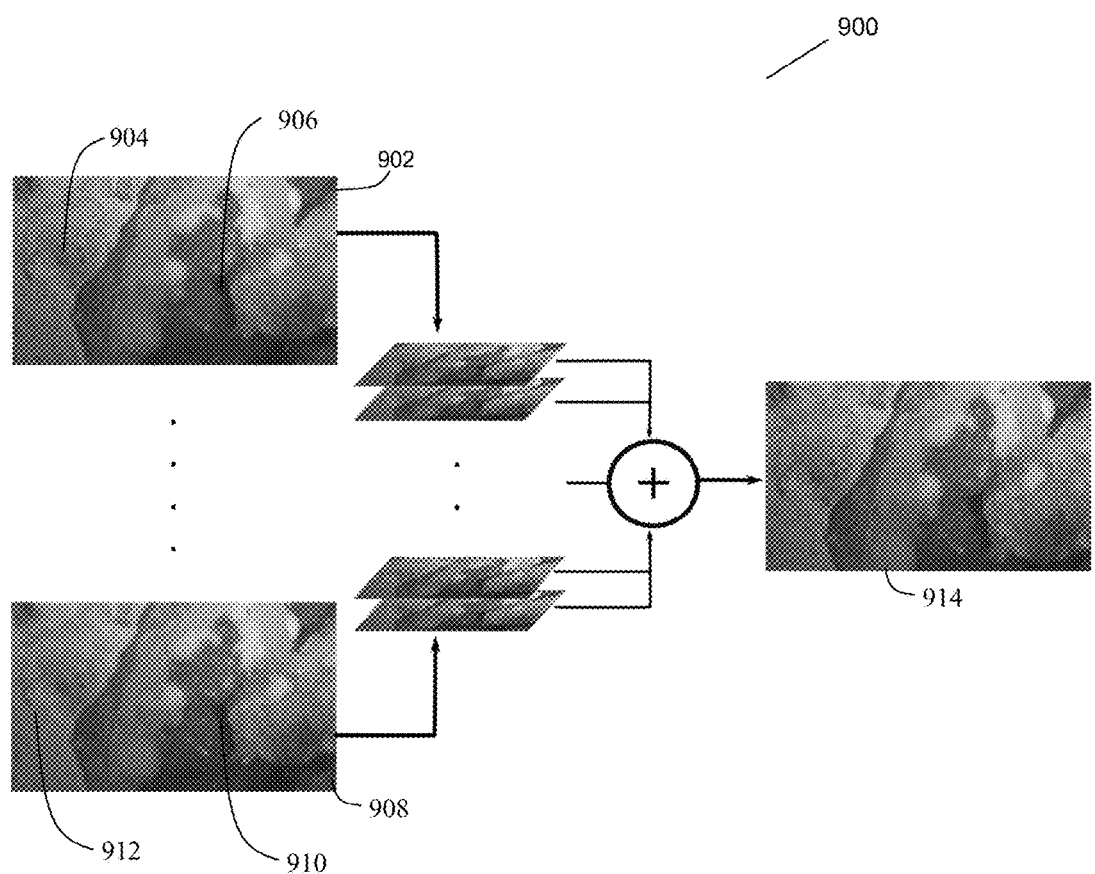
FIG. 9 is a diagram illustrating image stitching where focused regions of different depths may be stitched together into a composite image.

Referring now to FIG. 9, a diagram 900 is shown illustrating image stitching where focused regions of different depths may be stitched together into a composite image. In one example, one way to provide depth of field is to use focus planes to determine depth. In the process of doing this, the medical navigation system may acquire an image of the field having a focus at each depth plane, as discussed above. A first image 902 may be acquired where some of the surgical field of view is in focus, or at least a first portion 904 of the first image 902 is in focus and a second portion 906 of the first image 902 may be out of focus. Further, a second image 908 may be acquired where some of the surgical field of view is in focus, or at least a second portion 910 of the second image 908 is in focus and a second portion 912 of the second image 908 may be out of focus. Generating a depth map may provide for an artificial increase in the depth of field by stitching the focused regions of the different depths together and amalgamating these images into a composite image, indicated by 914, in which all or many parts of image are provided in the best focus. Image 914 illustrates examples of how composite images may be created using at least two focused regions 904, 910 that are stitched together. Such composite image creation may be beneficial for informatics or training purposes or may provide better images for the rest of the surgical team or spectators to view during a surgery.

One aspect of the present application provides a medical navigation system for acquiring a depth map of a surgical site of interest in a patient. The system comprises a camera for viewing the surgical site of interest and having a depth of field and an adjustable focus, a display, and a controller electrically coupled to the camera, the light projecting device, and the display. The controller has a processor coupled to a memory. The controller is configured to generate a signal to operate the camera to perform a focus sweep and capture a plurality of images during the focus sweep such that substantially all elements of the surgical site of interest are in focus in at least one of the plurality of images, receive from the camera data representing the plurality of images captured during the focus sweep; and generate a depth map of the surgical site of interest using the data representing the plurality of images by examining edge contrast in the plurality of images.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A medical navigation system for acquiring a depth map of a surgical site of interest in a patient, comprising:
a camera for viewing the surgical site of interest and having a depth of field and an adjustable focus,
a light projecting device for projecting an edge indicator on the surgical site of interest;
a display; and
a controller electrically coupled to the camera, the light projecting device, and the display, the controller having a processor coupled to a memory, the controller configured to:
generate a signal provided to the light projecting device to project the edge indicator on the surgical site of interest;
generate a signal to operate the camera to perform a focus sweep and capture a plurality of images during the focus sweep such that substantially all elements of the surgical site of interest are in focus in at least one of the plurality of images, the plurality of images including the projected edge indicator;
receive from the camera data representing the plurality of images captured during the focus sweep;
generate a depth map of the surgical site of interest using the data representing the plurality of images;
generate a signal to operate the camera to capture a live video feed of the surgical site of interest while a surgical procedure is being performed;
receive from the camera data representing the live video feed;
cause the display to display the live video feed; and
cause the display to display the depth map, the depth map being overlaid on the live video feed, the depth map including a series of contour lines.

2. The medical navigation system according to claim 1, wherein the controller is further configured to:
save the data representing the plurality of images in the memory; and
save the generated depth map in the memory.

3. The medical navigation system according to claim 1, wherein the projected edge indicator is projected using one of visible light, invisible light, infrared light, and ultraviolet light.

4. The medical navigation system according to claim 1, wherein the projected edge indicator includes a plurality of horizontal parallel lines and a plurality of vertical parallel lines each perpendicular to the plurality of horizontal parallel lines, the plurality of horizontal parallel lines and the plurality of vertical parallel lines arranged in a grid pattern.

5. The medical navigation system according to claim 1, wherein the depth map of the surgical site of interest is generated using the data representing the plurality of images by analyzing image sharpness of features of each of the plurality of images based on the focus depth of each of the plurality of images.

6. The medical navigation system according to claim 5, wherein the depth map of the surgical site of interest is further generated by analyzing sharpness of intersecting perpendicular and horizontal lines in a grid pattern in the plurality of images.

7. The medical navigation system according to claim 1, wherein the depth map of the surgical site of interest is generated by analyzing polarization of light reflected from the surgical site of interest.

8. The medical navigation system according to claim 1, wherein the focus sweep is performed in response to an input provided to the controller using an input device coupled to the controller.

9. The medical navigation system according to claim 1, wherein the light projecting device projects the light through the camera.

10. The medical navigation system according to claim 1, wherein the camera includes a videoscope.

11. The medical navigation system according to claim 1, wherein the controller is further configured to:
stitch the focused regions from at least two of the plurality of images together to generate a composite image.

12. A method of acquiring a depth map of a surgical site of interest in a patient, the method performed on a medical navigation system having a camera, a light projecting device, a display, and a controller electrically coupled to the camera, the light projecting device, and the display, the controller having a processor coupled to a memory, the method comprising:

projecting with the light projecting device an edge indicator on the surgical site of interest;

performing with the camera a focus sweep and capturing a plurality of images during the focus sweep such that substantially all elements of the surgical site of interest are in focus in at least one of the plurality of images, the plurality of images including the projected edge indicator;

receiving at the controller from the camera data representing the plurality of images captured during the focus sweep;

generating a depth map of the surgical site of interest using the data representing the plurality of images;

capturing with the camera a live video feed of the surgical site of interest while a surgical procedure is being performed;

receiving at the controller from the camera data representing the live video feed; displaying on the display the live video feed; and displaying the depth map on the display, the depth map being overlaid on the live video feed, the depth map including a series of contour lines.

13. The method according to claim 12, further comprising:

saving the data representing the plurality of images in the memory;

and saving the generated depth map in the memory.

14. The method according to claim 12, wherein the projected edge indicator is projected using one of visible light, invisible light, infrared light, and ultraviolet light.

15. The method according to claim 12, wherein the projected edge indicator includes a plurality of horizontal parallel lines and a plurality of vertical parallel lines each perpendicular to the plurality of horizontal parallel lines, the plurality of horizontal parallel lines and the plurality of vertical parallel lines arranged in a grid pattern.

16. The method according to claim 12, wherein the depth map of the surgical site of interest is generated using the data representing the plurality of images by analyzing image sharpness of features of each of the plurality of images based on the focus depth of each of the plurality of images.

17. The method according to claim 16, wherein the depth map of the surgical site of interest is further generated by analyzing sharpness of intersecting perpendicular and horizontal lines in the grid pattern in the plurality of images.

18. The method according to claim 12, wherein the depth map of the surgical site of interest is generated by analyzing polarization of light reflected from the surgical site of interest.

19. The method according to claim 12, wherein the focus sweep is performed in response to an input provided to the controller using an input device coupled to the controller.

20. The method according to claim 12, wherein the light projecting device projects the light through the camera.

21. The method according to claim 12, wherein the camera includes a videoscope.

22. The method according to claim 12, further comprising:

stitching focused regions from at least two of the plurality of images together to generate a composite image.

23. A medical navigation system for acquiring a depth map of a surgical site of interest in a patient, comprising:

a camera for viewing the surgical site of interest, a light projecting device for projecting an edge indicator on the surgical site of interest, the light projecting device having an adjustable focus plane;

a display; and a controller electrically coupled to the camera, the light projecting device, and the display, the controller having a processor coupled to a memory, the controller configured to:

generate a signal provided to the light projecting device to project the edge indicator on the surgical site of interest and perform a focus sweep of the light projecting device over a range of the adjustable focus plane, the surgical site of interest having a surface contour with a maximum elevation and a minimum elevation and the sweep of the adjustable focus plane spanning a range from the minimum elevation to the maximum elevation;

generate a signal to operate the camera and capture a plurality of images during the focus sweep of the light projecting device, the plurality of images including the projected edge indicator;

receive from the camera data representing the plurality of images captured during the focus sweep; and generate a depth map of the surgical site of interest using the data representing the plurality of images.

* * * * *